United States Patent [19]

Levin et al.

[11] E Patent Number: Re. 32,922

[45] Reissued Date of Patent: May 16, 1989

[54] BLOOD SAMPLING INSTRUMENT

[75] Inventors: Paul D. Levin, 1595 Soquel Dr., Santa Cruz, Calif. 95065; John D. Harding, Santa Cruz, Calif.

[73] Assignee: Paul D. Levin, Santa Cruz, Calif.

[21] Appl. No.: 33,252

[22] Filed: Apr. 2, 1987

Related U.S. Patent Documents

Reissue of:

[64] Patent No.: 4,517,978
Issued: May 21, 1985
Appl. No.: 442,600
Filed: Jan. 13, 1983

[51] Int. Cl.[4] ..... A61B 17/34

[52] U.S. Cl. ..... 128/314; 128/329 R; 604/131

[58] Field of Search ..... 128/314, 315, 329 R, 128/333, 770; 604/136, 137, 157

[56] References Cited

U.S. PATENT DOCUMENTS

| | | | |
|---|---|---|---|
| 361,750 | 4/1887 | Dunbar . | |
| 677,756 | 7/1901 | Caldwell . | |
| 922,331 | 5/1909 | Quarles . | |
| 2,295,849 | 9/1942 | Kayden . | |
| 2,472,116 | 6/1949 | Maynes . | |
| 2,531,267 | 11/1950 | Harnisch . | |
| 2,671,448 | 3/1954 | Harnisch . | |
| 3,166,069 | 1/1965 | Enstrom et al. . | |
| 3,656,472 | 4/1972 | Ben Moura . | |
| 3,659,610 | 5/1972 | Cimber . | |
| 3,797,483 | 3/1974 | Hurschman et al. . | |
| 3,809,095 | 5/1974 | Cimber . | |
| 3,880,163 | 4/1975 | Ritterskamp . | |
| 3,892,237 | 7/1975 | Steiner . | |
| 4,139,011 | 2/1979 | Benoit et al. | 128/329 R |
| 4,360,016 | 11/1982 | Sarrine | 128/329 R X |
| 4,375,815 | 3/1983 | Burns | 128/314 |
| 4,379,456 | 4/1983 | Cornell et al. | 128/314 |
| 4,384,579 | 5/1983 | Lucas | 604/136 X |
| 4,388,925 | 6/1983 | Burns | 128/314 |
| 4,403,989 | 9/1983 | Christensen et al. . | |
| 4,449,529 | 5/1984 | Burns et al. . | |
| 4,487,602 | 12/1984 | Christensen et al. . | |
| 4,503,856 | 3/1985 | Cornell et al. . | |
| 4,512,767 | 4/1985 | Denance . | |
| 4,527,561 | 7/1985 | Burns . | |
| 4,616,649 | 10/1986 | Burns . | |
| 4,624,253 | 11/1986 | Burns . | |

OTHER PUBLICATIONS

Sutor A. H. et al., "Bleeding From Standardized Skin Punctures: Automated Technic for Recording Time, Intensity and Pattern of Bleeding", *Amer. J. Clin. Path.*, 55: 541-550, 1971.

*Primary Examiner*—Edward M. Coven

[57] ABSTRACT

A blood sampling instrument for drawing a few drops of blood from a finger or the like is provided wherein the sampling device consists primarily of a tubular member which conceals all of the working parts and which has a flange thereon so that it can be easily held by a patient and pressed against a finger while releasing a trigger mechanism to actuate a plunger within the instrument.

10 Claims, 1 Drawing Sheet

BLOOD SAMPLING INSTRUMENT

Matter enclosed in heavy brackets [ ] appears in the original patent but forms no part of this reissue specification; matter printed in italics indicates the additions made by reissue.

*This application is a reissue of Ser. No. 06/442,600 filed on Jan. 13, 1983 which is now U.S. Pat. No. 4,517,978.*

SUMMARY OF THE INVENTION

The present invention relates to a blood sampling instrument for drawing a few drops of blood from a finger or the like. Such instruments are commonly used to draw blood samples for analytical purposes and particularly are used by diabetics who must monitor glucose levels.

A number of instruments have been proposed in the past but none has been fully satisfactory. Some instruments have been hard to hold and to maintain in a proper position while actuating a trigger. The device of the present invention has an annular flange thereon so that it can be easily held in the hand and pressed against a finger. A trigger is provided adjacent to the flange so that it is easy to disengage the plunger, carrying a needle, while the device is pressed against a finger.

Other devices have had moving parts which are exposed. This tends to scare the patient and also, if certain parts are exposed, they may rub against a patient's hand, unless care is taken, which will slow down the action of the plunger, preventing proper penetration.

Other devices which have been proposed have multiple triggers which must be simultaneously pressed while the device of the present invention has only a single trigger button so that it is easy to use and can be held in either hand. This is particularly advantageous for lefthanded patients.

Another advantage of the present invention is that the flange which the patient engages is fairly close to the tip so that the accuracy and sureness of placement are greater.

Another advantage of the present invention is the tip is heldly securely by threads but it is easy to remove if desired. Thus, it is easy to change the needle assembly. Further, since the tip or nosepiece can be made in various sizes, it is easy to provide replaceable tips suitable for either adults or children.

A further advantage of the present invention is it has a tubular sheath which both cocks the device and shields the plunger so that the patient's hand cannot absorb energy from the movement of the plunger, which might prevent proper skin penetration. The sheath is provided with a detent to give a positive indication that it has been fully retracted after a cocking operation.

A still further advantage of the present invention is the employment of a bounce back spring so that once the needle penetrates, it is immediately retracted, keeping it clean, safe and out of the way.

Other features and advantages of the invention will be brought out in the balance of the specification.

DESCRIPTION OF THE PREFERRED EMBODIMENT

Figure 1:
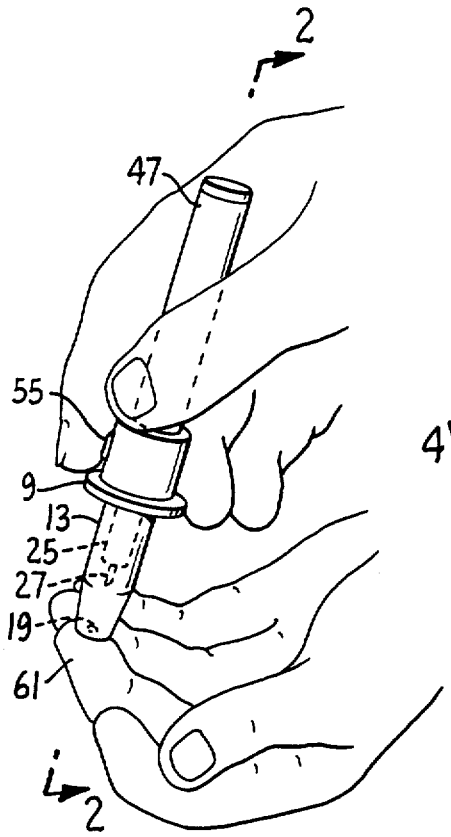
FIG. 1 is a perspective view of a device embodying the present invention showing it in use by a patient.

Referring now to the drawings by reference characters, the device of the present invention includes a fixed tubular member 5 which has an annular collar 7 attached thereto as well as an annular flange 9 located at the forward or distal end of the instrument. The forward portion of the member 5 is threaded as at 11 for the reception of a hollow nosepiece 13. Nosepiece 13 is tapered towards the front as at 15 and has a generally flat or slightly curved forward surface 17 with a small central hole 19.

Slidably mounted within the tubular member 5 is a plunger member 21 which has a socket 23 at its forward end for receiving a needle holder 25 which in turn holds the needle proper 27. A combination of parts 25 and 27 is a standard item available on the market, one brand of which is sold under the trade name of MONOLET.

Figure 4:
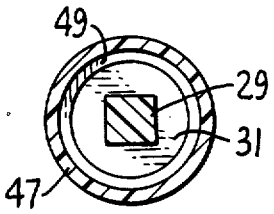
FIG. 4 is a section on the line 4—4 of FIG. 2.

Plunger 21 has a square shaft 29 extending to the rear and this passes through a square opening in an abutment 31 which is formed as part of the tubular member 5. This is best seen in FIG. 4; the square shaft prevents rotation of the plunger. The plunger 21 also has a small finger 33 which is adapted to extend into and be engaged in a hole 35 in the tubular member 5. A main spring 37 which extends between the shoulder 31 of the tubular member 5 and a shoulder 39 formed on plunger 21 tends to bias the plunger 21 towards the forward end of the instrument, i.e. down in FIGS. 2 and 3. At the rear of the shaft 29 is a collar 41 having a flange 43 which retains a bounce back spring 45.

Slidably mounted on the member 5 is an outer sleeve 47 which has an inturned abutment 49. Sleeve 47 also has a small projection 51 which fits into a mating notch 53 in the tubular member 5, the function of which will be later described.

A trigger 55 having a pin 57 is slidably mounted in collar 7 with the pin being adapted to press against finger 33 and push it down through the hole 35.

Action of the device will now be described. When the device is cocked, it is in the position shown in FIG. 2 with spring 37 compressed between shoulders 31 and 39. One presses the nosepiece 13 against a finger 61 by placing the fingers of the other hand against the flange 9 to insure good contact between the nosepiece 13 and finger 61. Now one presses trigger 55 which pushes the finger 33 out of the hole 35 so that the main spring, acting against the shoulder 39, pushes the plunger out to the position shown in FIG. 3 wherein the needle 27 momentarily extends out of the hole 19 and into the finger 61. This movement is in the direction shown by arrow 63. As this happens, bounce back spring 45 is compressed which causes plunger 21 to spring back slightly in the direction shown by arrow 65 so that the needle 27 is withdrawn through the hole 19 so that it is kept clean and out of the way. It will be noted that during this operation, there was no external movement of any of the parts. The patient was not aware of the movement of the needle, nor is it possible that the plunger might brush against the patient and slow down the action of the plunger.

Figure 2:
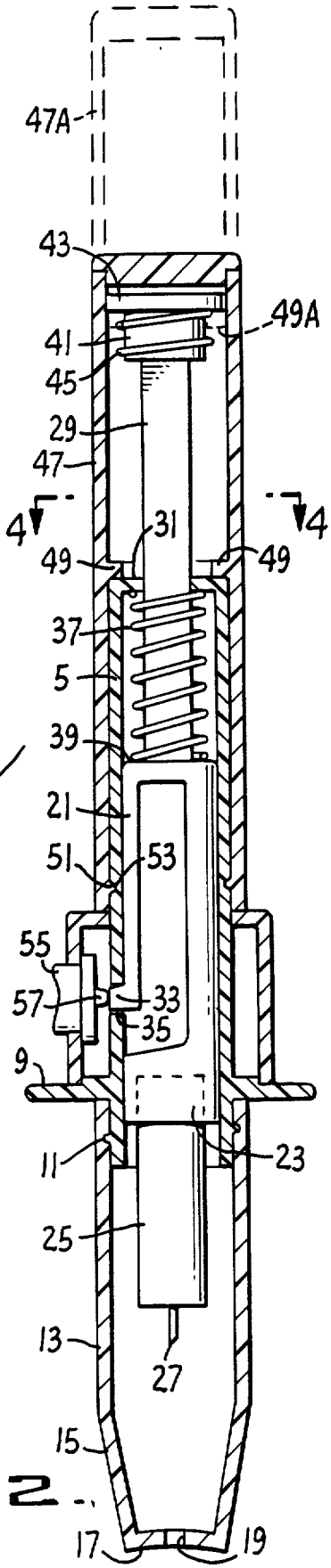
FIG. 2 is an enlarged side view, partly in section on the line 2—2 of FIG. 1 showing the device in cocked position in solid lines and the movement of the outer sheath in phantom during a cocking operation.
Figure 3:
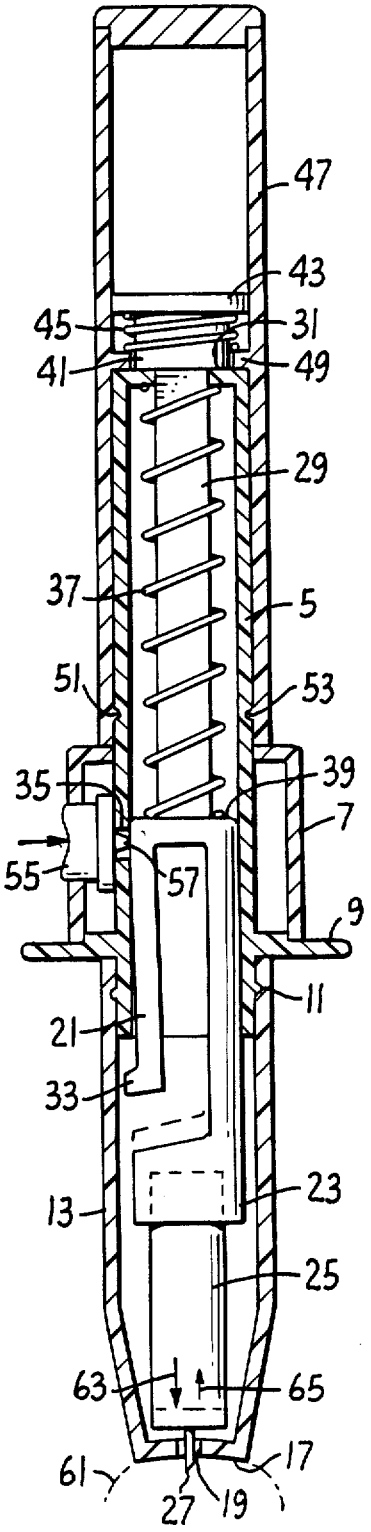
FIG. 3 is a view similar to FIG. 2 showing the device just after it has been operated.

When one wishes to operate the device, the main spring 37 is again cocked, as is shown in phantom in FIG. 2. One pulls back on sleeve 47 to the position shown at 47A. This moves abutment 49 to the position shown in phantom at 49A pushing against flange 43, thus pulling back plunger 21 at which time the finger 33 engages in and is held by the hole 35 so that the spring 37 is now again compressed. This leaves the sleeve 47 free and the patient can now push it back down against the collar 7. The detent 51 engaging in the notch 53 gives a little "click" as the sleeve is pushed back down into the rest position, giving the patient both an audible and tactile indication that the sleeve has been fully returned to rest position and will not interfere with the next operation. Also, the detent serves to hold the sleeve in place and to not allow it to freely slide up and down. At the same time, button 55 is raised so that the patient can tell at a glance that the device is cocked and ready for a repetition of the operation.

It was previously mentioned that the nosepiece 13 is threadably mounted by means of threads 11 on the tubular member 5. Thus, it is easy to remove the nosepiece 13 for cleaning or replacement of the needle assembly 25 and 27. Also, the nosepiece can be made in various sizes so that one can secure deep penetration for an adult or relatively shallow penetration for a child.

Many variations can be made in the exact structure shown without departing from the spirit of this invention. [

We claim] *What is claimed is:*

1. A blood sampling instrument designed to be hand held by an operator and being adapted to prick a finger or the like of a patient to draw a few drops of blood, said instrument having a distal end toward a patient and a proximal end toward an operator, comprising in combination:

[(a)] a tubular member having a hollow nosepiece at the distal end with an aperture at the terminal end thereof and a spring chamber at the proximal end,

[(b)] an annular collar having a shoulder at the proximal end thereof and an annular flange immediately behind said nosepiece at the distal end of said collar,

[(c)] a hollow sleeve surrounding said spring chamber,

[(d)] a plunger mounted for reciprocation within said tubular member,

[(e)] a shoulder within said tubular member, a main spring mounted within said spring chamber, said shoulder engaging said spring and biasing said plunger toward said nosepiece,

[(f)] a socket and a needle mounted therein on the distal end of said plunger,

[(g)] an aperture on the side of said tubular member, a finger on said plunger to engage said aperture and hold said plunger when said plunger is drawn away from said nosepiece,

[(h)] a trigger button extending from said collar and having means to engage the finger on said plunger,

[(i)] plunger cocking means on said sleeve to pull said plunger away from said nosepiece and engage said finger whereby

[(j)] the nosepiece of said instrument can be pressed against a finger by exerting pressure on said flange while pressing said trigger to release said plunger and cause said needle to be driven out of said nosepiece.

2. The instrument of claim 1 having mounting means on said tubular member for said sleeve whereby said sleeve can be retracted to lie against said shoulder after a cocking operation permitting said sleeve to remain stationary when said plunger is released and protecting the plunger from contact with the holding hand.

3. The instrument of claim 2 having a projection on said sleeve and a mating notch in the tubular member to provide a click stop when said sleeve is fully retracted to give an audible and tactile indication that the sleeve is retracted and to restrain the sleeve against easy sliding movement.

4. The instrument of claim 1 having a bounce back spring on the proximal end of said plunger whereby said needle is drawn back into the nosepiece after initially extending beyond the nosepiece.

5. The instrument of claim 1 having detachable mounting means on said tubular member for said nosepiece whereby nosepieces of different lengths can be mounted on said tubular member.

*6. A lancet designed to be hand-held by an operator to prick a finger or the like comprising in combination:*

*a plunger assembly;*

*means including a two-part assembly for housing said plunger assembly and comprising a tubular member and a tubular sleeve, one received within the other for relative sliding and reciprocating movement;*

*said plunger assembly including a trigger mechanism reciprocably movable within said two-part assembly;*

*a nosepiece detachably mounted to one end of said tubular member;*

*a needle assembly detachably mounted to one end of said plunger assembly and housed within said nosepiece;*

*a spring mounted within said two-part assembly and seated within said tubular member for biasing said plunger assembly toward said nosepiece;*

*said trigger mechanism having a detent engageable with said tubular member when said plunger assembly occupies a position of retraction against said spring; and*

*means formed on said plunger assembly and contained within said tubular sleeve limiting movement of said plunger assembly relative to said tubular sleeve;*

*whereby axial movement of said tubular sleeve in one direction relative to said tubular member moves said plunger assembly against the bias of said spring into a cocked position, said sleeve thereafter being axially moved in the opposite direction relative to said plunger assembly into a position for releasing said detent, and*

*whereby subsequent operation of said detent releases it from engagement with said tubular member allowing said spring to move said plunger assembly and thrust said needle assembly through said nosepiece.*

*7. The lancet of claim 6 and further comprising a trigger button for engaging said detent, and an annular collar mounted to said tubular member and defining a recess for retaining said trigger button, said collar also providing a stop that is engaged by said tubular sleeve in its position for releasing said detent.*

*8. The lancet of claim 6 and further comprising a flange mounted on the end of said tubular member adjacent said nosepiece.*

*9. The lancet of claim 6 and further comprising a bounce back spring interposed between said plunger assembly and said tubular sleeve, whereby said needle assembly is withdrawn into said nosepiece after being extended therethrough following release of said detent.*

*10. A blood sampling instrument designed to be hand-held by an operator to prick a finger or the like, said instrument comprising in combination:*

*a tubular member having a spring chamber at one end and a trigger chamber at its other end,*

*a tubular sleeve sidably mounted over and along the one end of said tubular member,*

*a hollow nosepiece detachably mounted on the other end of said tubular member,*

*first means formed on said tubular member and said tubular sleeve for limiting relative axial movement therebetween,*

*a plunger assembly mounted within and housed by said tubular member and tubular sleeve, said assembly including a resilient trigger finger having a detent,*

*second means formed on said tubular sleeve and plunger assembly that allows limited relative axial movement therebetween,*

*said first and second means interacting to allow retraction of said plunger assembly as said tubular sleeve is moved along said tubular member away from said nosepiece,*

*third means formed in said tubular member for engaging said detent and retaining said plunger assembly in a cocked position,*

*a trigger button mounted on said tubular member for releasing said detent from engagement with said third means,*

*a spring mounted within the spring chamber of said tubular member, one end of said spring being seated in said chamber, the other end engaged with said plunger assembly biasing said plunger assembly in the direction of said nosepiece,*

*and a needle assembly detachably mounted to the end of said plunger assembly and housed in said nosepiece,*

*whereby said plunger assembly is housed within said tubular member and tubular sleeve and is set to a cocked position by their relative reciprocation, said plunger assembly and needle assembly being driven in the direction of said nosepiece upon release of said detent.*

* * * * *